(12) United States Patent
Lampert et al.

(10) Patent No.: US 10,485,415 B2
(45) Date of Patent: Nov. 26, 2019

(54) CONFOCAL IMAGING USING ASTIGMATISM

(71) Applicant: Align Technology, Inc., San Jose, CA (US)

(72) Inventors: Erez Lampert, Rehovot (IL); Isaia Glaser-Inbari, Givatayim (IL)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 16/163,432

(22) Filed: Oct. 17, 2018

(65) Prior Publication Data

US 2019/0046026 A1 Feb. 14, 2019

Related U.S. Application Data

(63) Continuation of application No. 15/650,777, filed on Jul. 14, 2017, which is a continuation of application No. 13/684,096, filed on Nov. 21, 2012, now Pat. No. 9,717,402.

(51) Int. Cl.
*A61B 1/24* (2006.01)
*G01B 11/25* (2006.01)
*A61C 9/00* (2006.01)

(52) U.S. Cl.
CPC .............. *A61B 1/24* (2013.01); *A61C 9/0066* (2013.01); *G01B 11/25* (2013.01)

(58) Field of Classification Search
CPC .......... A61B 1/24; A61C 9/0066; G01B 11/25
See application file for complete search history.

(56) References Cited

U.S. PATENT DOCUMENTS

| 6,351,325 B1* | 2/2002 | Mandella | G02B 21/0056 359/210.1 |
| 2005/0128487 A1 | 6/2005 | Hill | |
| 2008/0013086 A1* | 1/2008 | Deck | G01J 3/02 356/328 |
| 2011/0002530 A1 | 1/2011 | Zhuang et al. | |
| 2012/0075425 A1* | 3/2012 | Thiel | A61B 5/0068 348/46 |

OTHER PUBLICATIONS

International Search Report and Written Opinion of InterNational Application No. PCT/IB2013/002566 dated May 14, 2014, 14 pages.
Restriction Requirement for U.S. Appl. No. 13/684,096, dated May 18, 2015, 5 pages.
Office Action for U.S. Appl. No. 13/684,096, dated Jul. 16, 2015, 10 pages.
Final Office Action for U.S. Appl. No. 13/684,096, dated Dec. 10, 2015, 10 pages.

(Continued)

*Primary Examiner* — Michael E Teitelbaum
(74) *Attorney, Agent, or Firm* — Lowenstein Sandler LLP

(57) ABSTRACT

An intraoral scanning device comprises a hand-held housing and a confocal imaging device disposed in the hand-held housing. The confocal imaging device has a predetermined astigmatic aberration disposed in a light path thereof to asymmetrically focus light in a predetermined manner, wherein the light is associated with an image of a portion of an object captured by the confocal imaging device.

19 Claims, 4 Drawing Sheets

(56) References Cited

OTHER PUBLICATIONS

Office Action for U.S. Appl. No. 13/684,096, dated Oct. 19, 2016, 10 pages.
Notice of Allowance for U.S. Appl. No. 13/684,096, dated Apr. 20, 2017, 4 pages.
Restriction Requirement for U.S. Appl. No. 15/650,777, dated Apr. 18, 2018, 9 pages.
Office Action for U.S. Appl. No. 15/650,777, dated Aug. 15, 2018, 5 pages.
Notice of Allowance for U.S. Appl. No. 15/650,777, dated Nov. 23, 2018, 5 pages.
Notice of Allowability for U.S. Appl. No. 15/650,777, dated Dec. 28, 2018, 4 pages.

* cited by examiner

CONFOCAL IMAGING USING ASTIGMATISM

RELATED APPLICATIONS

The present application is a continuation of U.S. patent application Ser. No. 15/650,777, filed Jul. 14, 2017, which is a continuation of U.S. patent application Ser. No. 13/684,096, filed Nov. 21, 2012, issued as U.S. Pat. No. 9,717,402, both of which are incorporated by reference herein.

BACKGROUND

The present disclosure is related generally to the field of 3D imaging and particularly 3D imaging useful in fields such as dentistry. More particularly, the present disclosure is related to methods, apparatuses, and devices for confocal imaging using astigmatism.

It may be valuable to perform 3D scans of objects for many purposes, such as record keeping, making duplicates, and/or modifying the resultant digital images for various purposes, such as improving a design of the object or for treatment purposes, for example, if the object is part of a human body. One example related to the field of dentistry is to use such a scanned digital image for either record keeping or for treatment purposes. Dental treatments may involve, for instance, restorative (e.g., prosthodontic) and/or orthodontic procedures.

Restorative and/or prosthodontic procedures may be designed to implant a dental prosthesis (e.g., a crown or bridge) in the intraoral cavity of a patient or to plan for veneers for a patient's teeth, for instance. Orthodontic procedures may include repositioning misaligned teeth and changing bite configurations for improved cosmetic appearance and/or dental function. Orthodontic repositioning can be accomplished, for example, by applying controlled forces to one or more teeth over a period of time.

With computing device-aided teeth treatment systems, an initial digital data set (IDDS) representing an initial tooth arrangement may be obtained. The IDDS may be obtained in a variety of ways.

For example, the patient's teeth may be imaged to obtain digital data using direct and/or indirect structured light, X-rays, three-dimensional X-rays, lasers, destructive scanning, computing device-aided tomographic images or data sets, magnetic resonance images, intra-oral scanning technology, photographic reconstruction, and/or other imaging techniques. The IDDS can include an entire mouth tooth arrangement, some, but not all teeth in the mouth, and/or it can include a single tooth.

DETAILED DESCRIPTION

Figure 1:
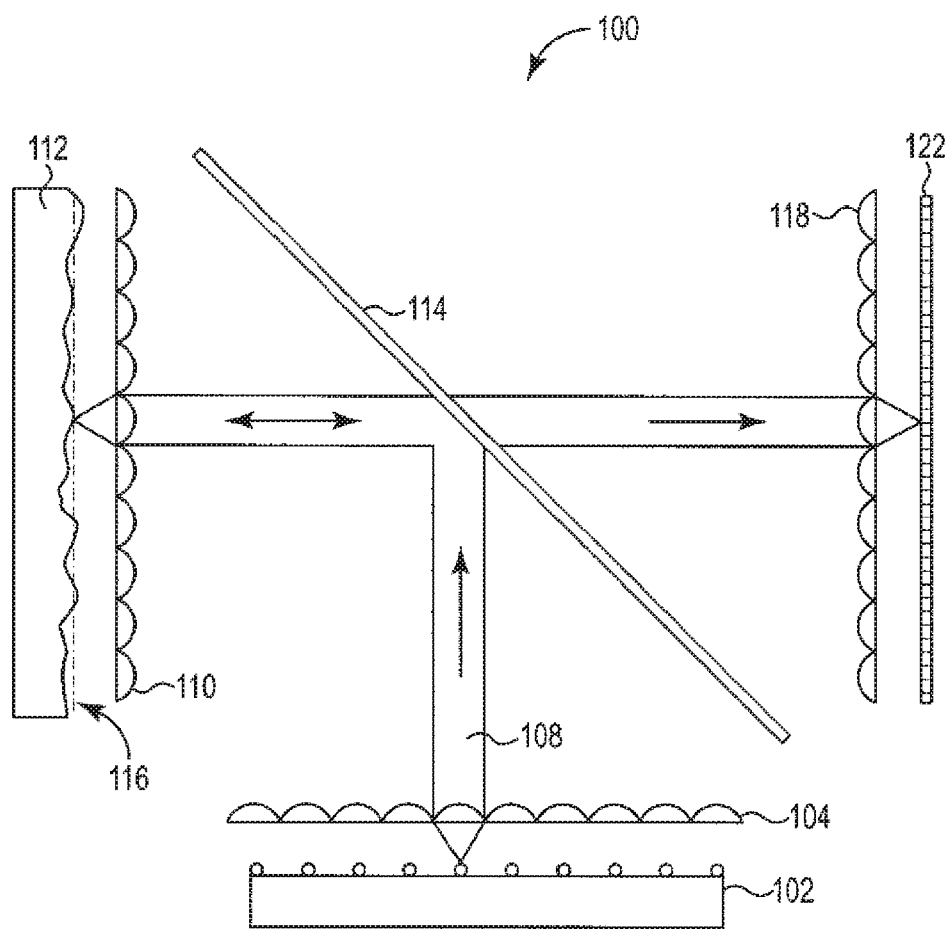
FIG. 1 illustrates an apparatus including a confocal imaging device according to a number of embodiments of the present disclosure.

A number of objects (e.g., 3 dimensional objects) may be scanned, for example, using a parallel confocal imager (e.g., scanner). With such an imager, multiple frames can be captured, each frame creating a depth section of the measured space, for instance. Multiple depth sections can allow for renderings of 3D reconstructions of the object(s). 3D reconstructions can be used for various purposes, such as, for example, the creation of physical models of the scanned object. 3D reconstructions can be stored in memory and/or converted to various data formats. In various embodiments, a scanning system may be used to obtain digital data representing a patient's teeth in their then current position (i.e., at the time of the scan) which can be considered, as used herein, an initial digital data set (IDDS) representing an initial tooth arrangement. An IDDS can be used for dental records and/or treatment purposes, for instance.

Embodiments of the present disclosure can determine (e.g., measure and/or render) surface topology of various objects. Although various embodiments are described herein with respect to the context of dental imaging and/or treatment, embodiments of the present disclosure are not so limited and can be used in various contexts.

Various embodiments can determine a location of a particular portion (e.g., a point location of a surface) of an object over a range of distances between the portion and a focus plane of a confocal imaging device. Accordingly, embodiments of the present disclosure can reduce a number of positions at which the focus plane is placed with respect to the object during frame capture. It may be desirable to reduce a number of frames captured to obtain a particular level of scan precision, quality and/or performance. For example, in the practice of intra-oral scanning, reducing scan duration can increase patient comfort and/or satisfaction. Further, reducing scan duration can provide direct benefits to a treating professional by permitting a scan to be simpler and/or faster. While such a reduction can lessen time spent actually acquiring frames, it can additionally reduce computational and/or communication loads associated with scanning. A reduction in frame captures can quicken computation and/or simplify scanning processes. Such a reduction can improve methods of scanning while the scanner is moving with respect to the teeth, for instance.

Point image pattern (e.g., point spread function (PSF), referred to generally herein as "image pattern," can be a smallest pattern to which an optical system at a particular configuration focuses a beam of light (e.g., light originating from a point object) upon a two-dimensional surface perpendicular to a path of the light. In non-astigmatic systems, an image pattern (e.g., a well-focused image pattern) can be referred to as an Airy pattern. An Airy pattern can be considered to be the best focused spot of light that a perfect lens with a circular aperture can make, limited only by the diffraction of light, for instance.

Astigmatism, as used herein, refers to an instance in various optical systems where light rays propagating in two perpendicular planes (e.g., a tangential plane and a sagittal plane) exhibit different foci (focal planes). As a result, an image of a point object that is out-of-focus in an astigmatic system may have a noncircular and/or circularly asymmetric image pattern (e.g., an image pattern that is substantially oblong, elliptical, and/or oval-shaped). That is, an out-of-focus astigmatic image pattern has perpendicular (e.g., substantially perpendicular) axes of differing lengths.

For example, in a focused astigmatic system, as the system goes out-of-focus in a first direction (e.g., the object moves closer to the optical system) the image pattern may become elliptic with its major axis in a first orientation (e.g., horizontal). As the system goes out-of-focus in a second direction (e.g., the object moves away from the optical system), the image pattern may become elliptic with its major axis in a second orientation (e.g., vertical), perpendicular to the first orientation.

For an astigmatic image pattern, a ratio between the length of its major axis and the length of its perpendicular axis may relate to a value of the focus error (e.g., a distance from focus). The orientation of the major axis may relate to the direction of the focus error (e.g., whether the object is too far or too near).

Embodiments of the present disclosure may include a particular and/or predetermined astigmatic character. A particular astigmatic character can include an astigmatic character that causes light to form an image pattern in a particular and/or predetermined manner. A particular astigmatic character can be created by an astigmatic aberration in a light path of the optical system. Astigmatic aberrations include, for example, weak cylindrical lenses, toroidal optical surfaces (e.g., barrel and/or doughnut shaped surfaces), and/or the inclusion of a flat window having a surface oblique (e.g., not perpendicular) to an axis of the optical system, among others. Astigmatic aberrations, as referred to generally herein, can include devices causing an optical system to have an astigmatic character.

The present disclosure provides computing device implemented methods, apparatuses, and computing device readable media for confocal imaging using astigmatism. Such confocal imaging using astigmatism can include receiving an image of a portion of an object captured by a confocal imaging device having a particular astigmatic character, determining an image pattern associated with the image, and determining a distance between a focus plane of the confocal imaging device and the portion of the object based, at least in part, on information regarding the image pattern.

Confocal imaging using astigmatism can include scanning a surface of a three-dimensional object at a first scan setting with a scanner having a particular astigmatic character to obtain a first plurality of image patterns, wherein each image pattern of the first plurality corresponds to a respective portion of the surface, determining a first positional relationship between each respective portion and the scanner based on the first plurality of image patterns, scanning the surface of the three-dimensional object with the scanner at a second scan setting to obtain a second plurality of image patterns, determining a second positional relationship between each respective portion and the scanner based on the second plurality of image patterns, and generating data representative of a topology of the surface of the three-dimensional object based on the first positional relationships and the second positional relationships.

In some or all embodiments, an apparatus for confocal imaging using astigmatism can include a confocal imaging device having a predetermined astigmatic aberration disposed in a light path thereof to asymmetrically focus light in a predetermined manner, wherein the light is associated with an image of a portion of an object captured by the confocal imaging device.

Confocal imaging using astigmatism can also include receiving data representing an image pattern associated with an image of an object captured by a confocal imaging device having a particular astigmatic character and having an image sensor with a plurality of pixels, and determining a positional relationship between the object and a focus plane of the confocal imaging device based on a distribution of the diffraction pattern over a portion of the plurality of pixels.

In the detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure. As used herein, "a number of" a particular thing can refer to one or more of such things (e.g., a number of pixels can refer to one or more pixels).

The figures herein follow a numbering convention in which the first digit or digits correspond to the drawing figure number and the remaining digits identify an element or component in the drawing. Similar elements or components between different figures may be identified by the use of similar digits. For example, 100 may reference element "00" in FIG. 1, and a similar element may be referenced as 400 in FIG. 4. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention, and should not be taken in a limiting sense.

FIG. 1 illustrates an apparatus including a confocal imaging device 100 according to a number of embodiments of the present disclosure. Confocal imaging device 100 can be a hand-held intraoral scanner, for instance; though, as previously discussed, the present disclosure is not limited to dental applications and/or embodiments. As shown in FIG. 1, confocal imaging device 100 can include a light source array 102, a source lenslet array 104, a beam splitter 114, an object lenslet array 110, an image lenslet array 118, and an image sensor 122.

Confocal imaging devices in accordance with the present disclosure are not limited to the components illustrated in FIG. 1. Various arrangements calculated to achieve the same techniques can be substituted for the embodiment illustrated in FIG. 1. For example, embodiments of the present disclosure can include components not illustrated in FIG. 1 (e.g., a housing, etc.). Further, the number(s) of the various components illustrated in FIG. 1 are not to be taken in a limiting sense. For example, though light source array 102 is shown as including a particular number of light sources (e.g., ten), embodiments of the present disclosure are not limited to a particular number of light sources and/or light source arrays. A path traveled by light 108 through confocal imaging device 100, as illustrated in FIG. 1, may be herein referred to as a "light path."

An astigmatic aberration can be associated with (e.g., positioned at and/or within) various locations within the light path illustrated in FIG. 1 to create a particular astigmatic character in confocal imaging device 100. In various embodiments, an aberration can be adjacent to light source array 102 and/or associated with source lenslet array 104 (e.g., one or more lenslets in the light path between light source array 102 and beam splitter 114). In some or all embodiments, an aberration can be adjacent to image sensor 122 and/or associated with image lenslet array 118 (e.g., one or more lenslets in the light path between beam splitter 114 and image sensor 122). As discussed herein, an astigmatic aberration can asymmetrically focus light 108 such that a particular asymmetric image pattern can be shone upon, and received by, image sensor 122. For purposes of illustration, the discussion herein of confocal imaging device 100 includes an astigmatic aberration associated with image lenslet array 118; though, as previously discussed, embodiments of the present disclosure are not so limited.

Light source array 102 in some or all embodiments can be and/or include various light sources, including, for example, continuous wave lasers, air ion lasers, semiconductor lasers, etc. Light source array 102 can include a number of individual light sources and/or a number of components configured to produce a number of light beams (e.g., 100,000 light beams). For example, a plurality of incident light beams can be produced at light source array 102 by splitting a parent beam. Light source array 102 can include a plurality of light emitters, each configured to emit a single light beam, for instance. Light source array 102 can include various refraction and/or diffraction components configured to produce a plurality of light beams. For purposes of illustration, a single light beam, light 108 (e.g., a portion of light emitted by light source array 102), is shown in FIG. 1, and its path through confocal imaging device 100 is discussed herein.

Source lenslet array 104 in some or all embodiments can collimate and/or focus light 108 via a number of lenslets (e.g., microlenses). Beam splitter 114 can selectively separate light 108. For example, depending on various properties of beam splitter 114, light 108 (e.g., all or part of light 108) can pass through beam splitter 114 unreflected, as discussed below, for instance.

Light 108 can be emitted from light source array 102 and be focused and/or collimated by source lenslet array 104. Thereafter, it can be reflected by (e.g., partially reflected by) beam splitter 114, focused by a respective lenslet in object lenslet array 110 to a point (e.g., near point) at focus plane 116. As illustrated in FIG. 1, focus plane 116 can be located at various positions with respect to portions of an object 112. Object 112 can be and/or include various objects, such as, for example, a tooth. Portions of object 112 can be nearer to, farther from, and/or equidistant from object lenslet array 110 than focus plane 116. Where a particular portion of object 112 illuminated by light 108 is equidistant from object lenslet array 110, it can be considered to be "on" focus plane 116. Light 108 reflecting from a portion of object 112 that is on focus plane 116 can be re-collimated (e.g., refocused) by object lenslet array 110. Light 108 reflecting from portions of object 112 that are not on focus plane 116 can diverge and/or converge depending on whether such portions are nearer to, and/or farther from, object lenslet array 110 than focus plane 116, for instance, in addition to various configurable settings of confocal imaging device 100.

Light 108 can reflect off of object 112, be re-collimated by object lenslet array 110, and can pass through (e.g., pass through unreflected) beam splitter 114 towards a respective lenslet of image lenslet array 118, where it can be collimated and/or focused onto (e.g., received by) a number of pixels of image sensor 122. Image sensor 122 can be a device (e.g., Charge Coupled Device (CCD), Complimentary Metal Oxide Semiconductor (CMOS), etc.) configured to convert an optical image (e.g., an image pattern associated with light 108) to an electronic signal via, for example, a number of pixels discussed further below in connection with FIGS. 2A and/or 2B. Once received by image sensor 122, light 108 (e.g., the image pattern associated with light 108) can, for example, be used for various determinations such as those discussed further below.

As previously discussed, various lenslets of image lenslet 118 can have a particular astigmatic character (e.g., aberration). Accordingly, converging and/or diverging incoming rays of light 108 reflected from object 112 can produce oblong and/or ellipse-like image patterns on a number of pixels of image sensor 122 (discussed further below in connection with FIGS. 2A and/or 2B). An orientation (e.g., direction) of a major axis of such ellipse-like image patterns may depend on whether light 108 is diverging or converging as it is received by image sensor 122. Accordingly, the orientation of the major axis, in various embodiments, can indicate a position, with respect to focus plane 116, of the particular portion of object 112 illuminated by light 108. For example, embodiments of the present disclosure can determine whether the illuminated portion of object 112 was closer to, or further from, object lenslet array 110 than focus plane 116.

Additionally, embodiments of the present disclosure can determine various intensities of light 108 received at each of a number of pixels of image sensor 122. Accordingly, embodiments of the present disclosure can determine a magnitude of a distance between a particular portion of object 112 and focus plane 116. A "positional relationship," as used herein, can refer to a distance between a particular portion of object 112 and focus plane 116 (or confocal imaging device 100), and/or whether the particular portion of object 112 is nearer to, farther from, and/or equidistant from object lenslet array 110 (or confocal imaging device 100) than focus plane 116.

A single beam of light (light 108) is illustrated in FIG. 1 as being emitted by light source array 102. In various embodiments, additional light beams can be emitted from light source array 102 and can be reflected at various locations along beam splitter 114 towards respective lenslets of object lenslet array 110. Thus, a number of portions of object 112 can be illuminated simultaneously, for instance, and a number of positional relationships can be determined along a surface of object 112. Such relationships can be used to generate data representative of a topology of the surface of object 112, for instance.

Focus plane 116 (sometimes generally referred to herein as "scan setting") can be adjusted during a scan using confocal imaging device 100. Such adjustment can be carried out in various manners. For example, a number of servo motors can be used to manipulate a number of the optical components of confocal imaging device 100 (e.g., object lenslet array 110). Adjusting can include moving confocal imaging device 100 towards and/or away from object 112. Adjusting can be programmed and/or performed in accordance with computer-executable instructions (discussed below) such that a plurality of scan settings are equally spaced and/or sequential, for instance. Further, embodiments of the present disclosure can include a plurality of focus planes (e.g., each associated with a respective light path); such focus planes can be adjusted simultaneously (e.g., by moving confocal imaging device 100) and/or individually, for instance.

Figures 2A, 2B:
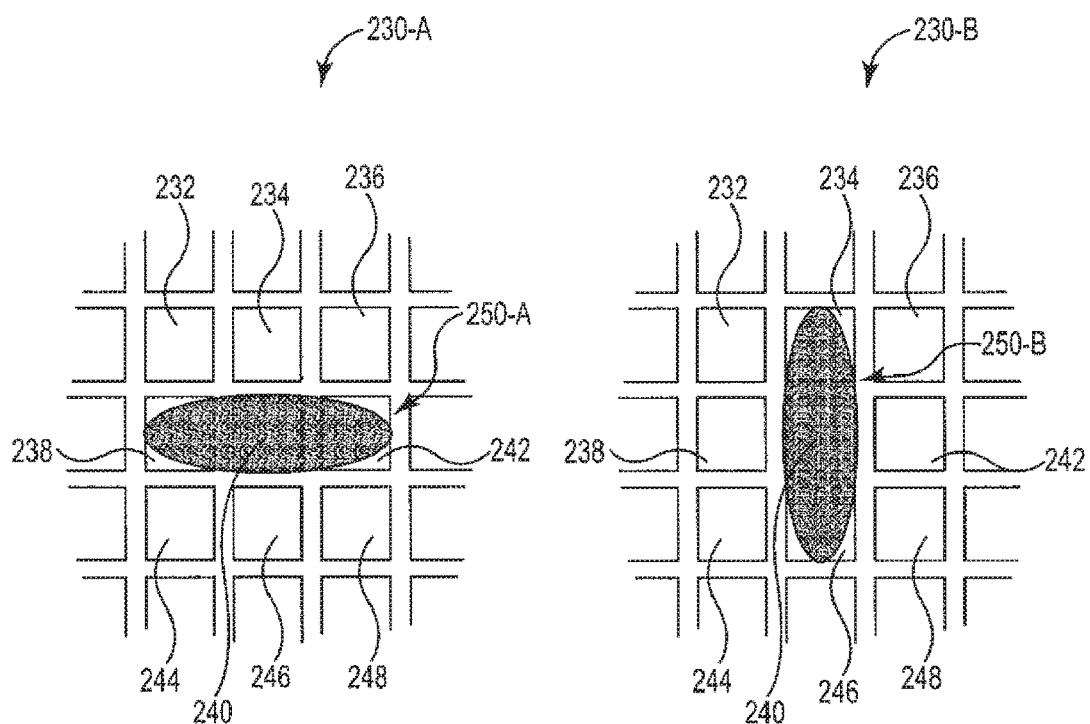
FIGS. 2A-2B illustrate a horizontal image pattern and a vertical image pattern, respectively, on a portion of an image sensor according to a number of embodiments of the present disclosure.

FIGS. 2A-2B illustrate a horizontal image pattern (e.g., distribution of light in an image of a point object) 250-A and a vertical image pattern 250-B, respectively, on a portion of an image sensor (portion 222-A and portion 222-B, respectively). Horizontal image pattern 250-A and vertical image pattern 250-B can represent situations in which an image is defocused (e.g., out-of-focus) in an astigmatic system (e.g., system 100 previously discussed in connection with FIG. 1). It is noted that FIG. 2A and FIG. 2B each illustrate single image patterns (e.g., associated with light 108) on a portion of an image sensor, though embodiments are not so limited. For example, multiple image patterns may be formed simultaneously on image sensors in accordance with the present disclosure.

As shown, horizontal image pattern 250-A and vertical image pattern 250-B are substantially oblong and/or ellipse-like, having perpendicular axes of differing lengths. Such shapes may be contrasted, for instance, with substantially circular defocused image patterns created by non-astigmatic systems.

FIG. 2A illustrates a portion 222-A of the image sensor (e.g., image sensor 122 previously discussed in connection with FIG. 1) receiving a horizontal image pattern 250-A. As shown in FIG. 2A, portion 222-A includes a number of pixels 232, 234, 236, 238, 240, 242, 244, 246, and 248, sometimes generally herein referred to as pixels 232-248. As shown in FIG. 2A, horizontal image pattern 250-A has a major axis oriented horizontally. Horizontal, as used herein, refers to a particular orientation and is used for illustrative purposes to indicate an orientation of a major axis of an image pattern with respect to a number of pixels of an image sensor.

It is noted that FIGS. 2A and 2B illustrate a particular number of pixels (e.g., nine pixels arranged in a 3×3 grid). However, embodiments of the present disclosure are not limited to a particular number of pixels. Similarly, embodiments of the present disclosure are not limited with respect to a number of pixels configured to receive an image pattern; rather, various numbers of pixels can be selected and/or arranged to receive image patterns.

FIG. 2B illustrates a portion 222-B of the image sensor illustrated in FIG. 2A receiving a vertical image pattern 250-B. As shown in FIG. 2B, portion 222-B includes the number of pixels 232-248. As shown in FIG. 2B, vertical image pattern 250-B has a major axis oriented vertically. Vertical, as used herein, refers to a particular orientation and is used for illustrative purposes to indicate an orientation of a major axis of an image pattern with respect to a number of pixels of an image sensor.

As shown in FIG. 2A, horizontal image pattern 250-A covers (e.g., light of image pattern 250-A strikes) pixel 240, and horizontal image pattern 250-A covers a portion of pixel 238 and a portion of pixel 242. As shown in FIG. 2B, vertical image pattern 250-B covers pixel 240 and a portion of pixel 234 and a portion of pixel 246. Pixels 232-248 can each contain a photo-detector and/or an active amplifier, among other circuitry, and can convert light energy (e.g., from image pattern 250-A and/or 250-B into an electric signal. Data from the electric signal can be saved in memory and/or processed by a computing device in a manner analogous to that discussed below, for instance.

Embodiments of the present disclosure can determine contextual information associated with defocused images based on orientations of image patterns. For example, horizontal image pattern 250-A may be received in a situation where an object (e.g., a portion of an object illuminated by a particular light beam) is proximal to a focal plane of a confocal imaging device (e.g., defocused in a first direction). For example, and with reference to FIG. 1, horizontal image pattern 250-A can indicate that an illuminated portion of object 112 is nearer to object lenslet array 110 than is focus plane 116.

Accordingly, vertical image pattern 250-B may be received in a situation where the object is beyond the focal plane of the confocal imaging device (e.g., defocused in a second direction). For example, and with reference to FIG. 1, vertical image pattern 250-B can indicate that object 112 is farther from object lenslet array 110 than is focus plane 116.

Confocal imaging devices according to the present disclosure in some or all embodiments are not limited to a particular configuration. Accordingly, image patterns are not limited to a particular orientation (e.g., horizontal and/or vertical). Further, relationships between orientations of image patterns and focal planes are not limited to the examples presented herein (e.g., horizontal image pattern 250-A can be associated with an object beyond the focus plane and vertical image pattern 250-B can be associated with an object proximal to the focus plane).

Embodiments of the present disclosure can differentiate between directions of defocus. As previously discussed, light rays in an astigmatic system propagate in two perpendicular planes having different focal lengths. The two focal lengths, $f_x$ and $f_y$, respectively, can refer to focal lengths of the vertical and horizontal image planes, though it is again noted that the illustrative use of "vertical" and "horizontal" herein merely indicates that the planes are perpendicular.

A distance S, can be defined as a distance between an object point and a front principle plane of an astigmatic lens. Another distance, $S_x'$, can be defined as a distance between a rear principle plane of the lens and the horizontal image plane (e.g., where the image pattern becomes nearly a vertical line). Another distance, $S_y'$, can be defined as a distance between the rear principle plane of the lens and the vertical image plane (e.g., where the image pattern becomes nearly a horizontal line). Accordingly:

$$\begin{cases} \dfrac{1}{f_x} = \dfrac{1}{S} + \dfrac{1}{S_x'} \\ \dfrac{1}{f_y} = \dfrac{1}{S} + \dfrac{1}{S_y'} \end{cases}$$

It is noted that if the lens discussed above is a substantially thin lens, both principle planes can merge into the plane of the lens itself.

If an image sensor is positioned at a distance $\tilde{S}$ from the rear principle plane, the size of the two axes of the resulting elliptical image pattern (e.g., of a point object) can be $d_x$ and $d_y$, given by:

$$\begin{cases} d_x \cong \left|\dfrac{\tilde{S} - S_x'}{S_x'}\right| D \\ d_y \cong \left|\dfrac{\tilde{S} - S_y'}{S_y'}\right| D \end{cases}$$

where D is a diameter of the lens. Values generated for $d_x$ and $d_y$ can be considered substantially accurate provided that $|\tilde{S} - S_x'|$ and $|\tilde{S} - S_y'|$ are substantially large relative to a light wavelength $\lambda$ (e.g., a wavelength of light 108).

Based on the non-astigmatic lens and image sensor relationships, astigmatic confocal depth (e.g., distance between the confocal imaging device and the object) can be determined. For example, a particular lenslet can be associated with a number of pixels of an image sensor (e.g., 3×3 pixels), numbered as:

$g_{m-1,n-1}$ $g_{m-1,n}$ $g_{m-1,n+1}$
$g_{m,n-1}$ $g_{m,n}$ $g_{m,n+1}$
$g_{m+1,n-1}$ $g_{m+1,n}$ $g_{m+1,n+1}$ where the $g_{m,n}$-th pixel is centered on the axis of the lenslet. The above matrix can be analogous to the arrangement of pixels 232-248 illustrated in FIGS. 2A and/or 2B, wherein, as shown, pixel 240 is centered in the axis of the lenslet. An intensity (e.g., a relative intensity) of the light received at the above pixels can correlate to a focus shift (e.g., a distance of the object from the focus plane). The intensity can be measured by an electric charge produced in the pixels, for instance. The electric charge, $e_{m,n}$, can be determined by:

$$e_{m,n} = \frac{(g_{m-1,n} + g_{m+1,n}) - (g_{m,n-1} + g_{m,n+1})}{\sum_{m'=m-1}^{m+1} \sum_{n'=n-1}^{n+1} g_{m',n'}}$$

The actual shift in the distance of the object, $\Delta S$, can be determined from the electric charge $e_{m,n}$ by theoretical calculation and/or by using a previously calculated look-up-table and/or interpolation function.

As the focus shift $\Delta S$ increases, the resulting image pattern may increase in size. In various embodiments, a particular increase in size may be avoided. For example, portions of the image pattern may cover (e.g., partially cover) adjacent pixels beyond the selected 3×3 pixels. Further, as the focus shift $\Delta S$ increases, an amount of light reaching each pixel may not exceed a particular threshold (e.g., may be insufficient for proper pixel reception). An image pattern can be limited in size through the conditions:

$$\begin{cases} \mu_{m,n} > \mu_{min} \\ \sigma_{m,n}^2 > \sigma_{min}^2 \end{cases}$$

where:

$$\sigma_{m,n}^2 = \frac{1}{9} \sum_{m'=m-1}^{m+1} \sum_{n'=n-1}^{n+1} (g_{m',n'} - \mu_{m,n})^2$$

$$\mu_{m,n} = \frac{1}{9} \sum_{m'=m-1}^{m+1} \sum_{n'=n-1}^{n+1} g_{m',n'}$$

and where $\sigma_{min}^2$ and $\mu_{min}$ can be pre-set threshold values, for instance.

Figure 3:
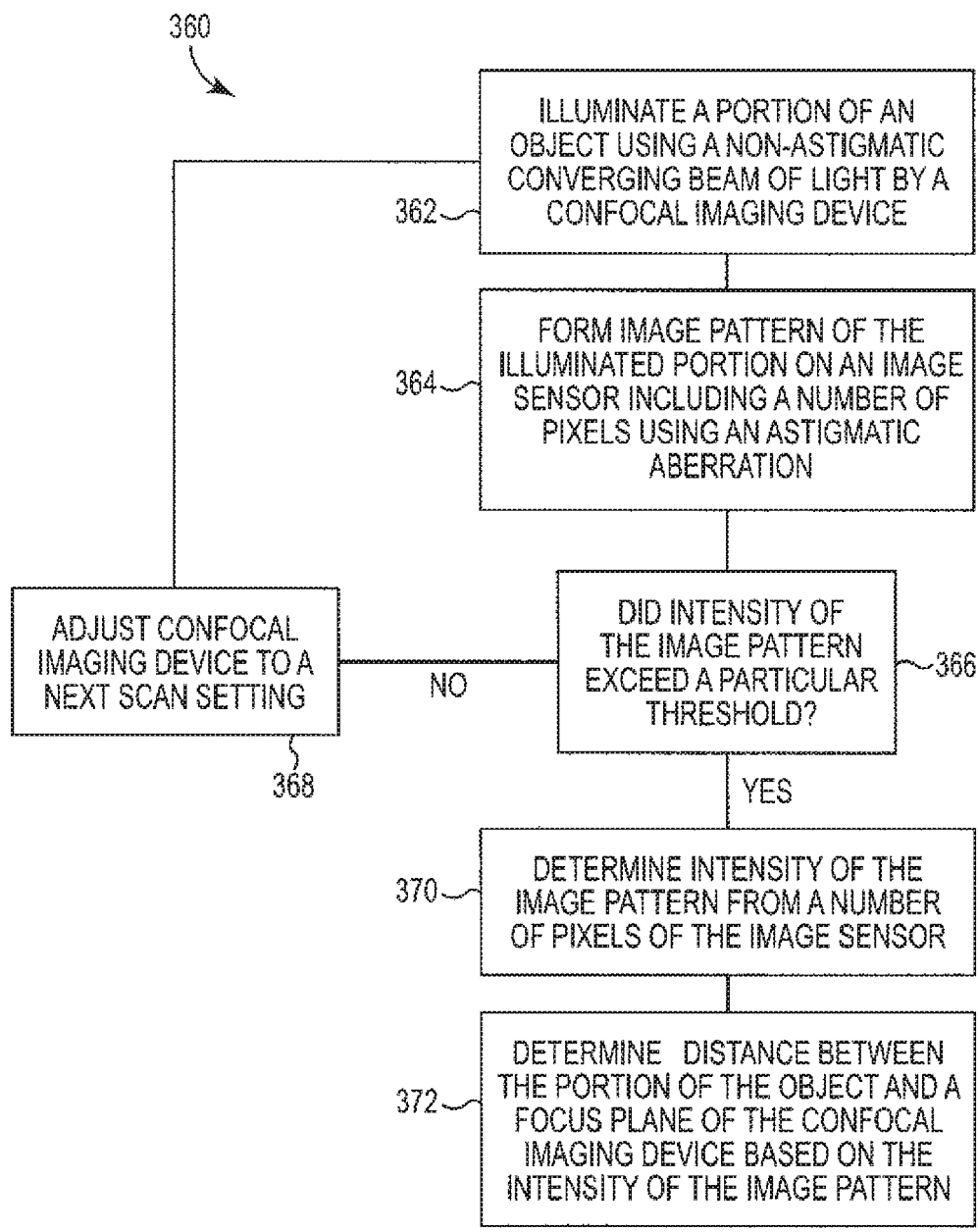
FIG. 3 is a flow chart illustrating a method for confocal imaging using astigmatism according to a number of embodiments of the present disclosure.

FIG. 3 is a flow chart illustrating a method 360 for confocal imaging using astigmatism according to a number of embodiments of the present disclosure. Method 360 can be performed by computing device 474, discussed below in connection with FIG. 4, for instance.

At block 362, a portion of an object (e.g., a surface of a three-dimensional object) can be illuminated using a non-astigmatic converging beam of light by a confocal imaging device (e.g., scanner) at a first scan setting. Such illumination can occur, for instance, as previously discussed in connection with FIG. 1 (e.g., illuminating a portion of object 112 with light 108). In various embodiments, and as previously discussed, multiple beams of light can be used to illuminate portions of the object. Accordingly, a surface of the three-dimensional object can be scanned with a scanner having a particular astigmatic character to obtain a first plurality of images at a first scan setting, wherein each image of the first plurality corresponds to a respective portion of the surface.

At block 364, an image pattern of the illuminated portion can be formed on an image sensor including a number of pixels using an astigmatic aberration. Such formation can be analogous to that previously discussed, for instance. In various embodiments, a first set of image patterns can be determined from a first plurality of images.

At block 366, a determination can be made regarding whether an intensity of the image pattern (e.g., an intensity of the light forming the image pattern) exceeds a particular threshold. A threshold can be associated with a particular electric charge produced by a number of pixels. Such a threshold can be user-determined, for instance, and/or based on various properties of the pixel(s) and/or associated circuitry. An intensity not exceeding the threshold may be insufficient for proper pixel reception, for instance, and may indicate that the portion of the object exceeds a particular distance from focus (e.g., too far from focus for an image pattern to be properly received).

At block 368, if a determination is made that the intensity did not exceed the threshold, the confocal imaging device can be adjusted to a next (e.g., second) scan setting (e.g., as discussed above) whereupon the object can be illuminated using the non-astigmatic converging beam of light at the second scan setting. Various embodiments using multiple light beams can include scanning a surface of a three-dimensional object at a first scan setting with a scanner having a particular astigmatic character to obtain a first plurality of image patterns, wherein each image pattern of the first plurality corresponds to a respective portion of the surface. Embodiments herein are not limited to a particular number of images and/or scan settings, nor are embodiments limited to a particular number of images captured per scan setting.

If, at block 366, the intensity of the image pattern was determined to have exceeded the threshold, an intensity of the image pattern (e.g., a level of electric charge of a pixel nearest to a center of the image pattern) can be determined from a number of pixels of the image sensor (e.g., as discussed above in connection with FIGS. 2A and/or 2B) at block 370. Various embodiments of the present disclosure include determining a second set of image patterns from the second plurality of images. Intensities of image patterns can be determined from (e.g., based on) various images at various scan settings.

Accordingly, at block 372, a distance between the portion of the object and a focus plane of the confocal imaging device (e.g., a positional relationship) can be determined based on information regarding the image pattern (e.g., the intensity of the image pattern). Such a determination can be made in a manner analogous to that previously discussed, for instance. Determining distances (e.g., a plurality of distances over a surface of the object) can include determining a first positional relationship between each respective portion and the scanner based on a first plurality of image patterns (e.g., received at the first scan setting).

Further, the scanner can be adjusted to a second scan setting and used to scan the surface of the three-dimensional object with at the second scan setting to obtain a second plurality of image patterns. A second positional relationship between each respective portion and the scanner can be determined based on the second plurality of image patterns. Data representative of a topology of the surface of the three-dimensional object can be generated based on the first positional relationships and the second positional relationships, for instance, though embodiments of the present disclosure are not limited to a particular number of scan settings, image patterns, and/or positional relationships used to generate such data.

Figure 4:
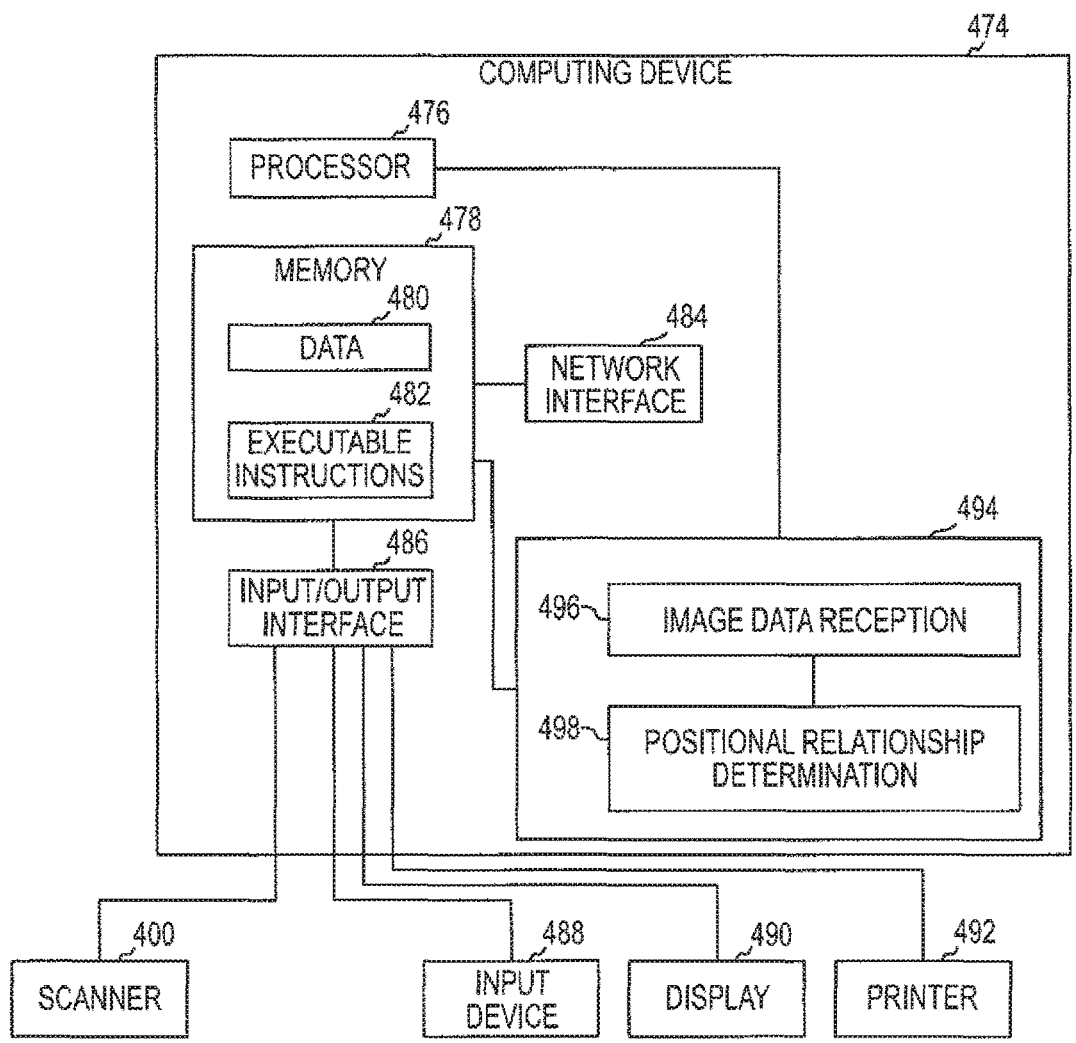
FIG. 4 illustrates a system for confocal imaging using astigmatism according to a number of embodiments of the present disclosure.

FIG. 4 illustrates a system for confocal imaging using astigmatism according to a number of embodiments of the present disclosure. The system illustrated in FIG. 4 can include a computing device 474 having a number of components coupled thereto. The computing device 474 can include a processor 476 and memory 478. The memory 478 can include various types of information including data 480 and executable instructions 482 as discussed herein.

The memory 478 and/or the processor 476 may be located on the computing device 474 or off the device in some embodiments. As such, as illustrated in the embodiment of FIG. 4, a system can include a network interface 484. Such an interface can allow for processing on another networked computing device or such devices can be used to obtain information about the patient or executable instructions for use with various embodiments provided herein.

As illustrated in the embodiment of FIG. 4, a system can include one or more input and/or output interfaces 486. Such interfaces can be used to connect the computing device 474 with one or more input or output devices.

For example, in the embodiment illustrated in FIG. 4, the system includes connectivity to a scanner 400 (e.g., a confocal imaging device as described herein), an input device 488 (e.g., a keyboard, mouse, etc.), a display device 490 (e.g., a monitor), and a printer 492. The input/output interface 486 can receive data 480, storable in the data storage device (e.g., memory 478), representing data corresponding to a number of images (e.g., of patient's dentition), among other data. In some embodiments, the scanner 400 can be configured to scan the patient's upper and/or lower jaws directly (e.g., intraorally).

The processor 476 in any or all embodiments can be configured to provide a visual indication of a virtual dental model on the display 490 (e.g., on a GUI running on the processor 476 and visible on the display 490). The processor 476 can further be configured (e.g., via computer executable instructions stored in a tangible non-transitory computer readable medium) to perform the various methods, algorithms, and/or functionality described herein. The processor 476, in association with the data storage device 478, can be associated with data and/or application modules 494. The processor 476, in association with the data storage device 478, can store and/or utilize data and/or execute instructions to provide a number of application modules for confocal imaging using astigmatism.

Such connectivity can allow for the input and/or output of virtual dental model information or instructions (e.g., input via keyboard) among other types of information. Although some embodiments may be distributed among various computing devices within one or more networks, such systems as illustrated in FIG. 4 can be beneficial in allowing for the capture, calculation, and/or analysis of information discussed herein.

A system for confocal imaging using astigmatism can include a scanning module and a processing module (e.g., processor 476). The scanning module can include an intraoral 3D confocal imaging scanner having a particular astigmatic character.

The processing module (e.g., processor 476) can (e.g., via application module 494) receive 496 data representing an image pattern associated with an image of an object captured by a confocal imaging device (e.g., confocal imaging device 100) having a particular astigmatic character and having an image sensor with a plurality of pixels. The processor 476 (e.g., via application module 494) can determine 498 a positional relationship between the object and a focus plane of the confocal imaging device based on a distribution of the diffraction pattern over a portion of the plurality of pixels, in a manner analogous to that previously discussed in connection with FIGS. 2A and/or 2B, for instance.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:
1. An intraoral scanning device, comprising:
   a hand-held housing;
   a confocal imaging device disposed in the hand-held housing, the confocal imaging device having a predetermined astigmatic aberration disposed in a light path thereof to asymmetrically focus light in a predetermined manner, wherein the light is associated with an image of a portion of an object captured by the confocal imaging device;

an image sensor disposed within the hand-held housing, the image sensor comprising a plurality of pixels, wherein the plurality of pixels are to receive the light associated with the image of the portion of the object, the light having a circularly asymmetric image pattern; and a computing device configured to determine a positional relationship between the portion of the object and a focus plane of the confocal imaging device based on a diffraction pattern over a portion of the plurality of pixels, wherein the diffraction pattern is associated with the circularly asymmetric image pattern.

2. The intraoral scanning device of claim 1, wherein the predetermined astigmatic aberration is associated with a lens of the confocal imaging device that is adjacent to the image sensor.

3. The intraoral scanning device of claim 1, wherein the computing device is configured to determine a distance between the confocal imaging device and the object based on the circularly asymmetric image pattern received by the image sensor.

4. The intraoral scanning device of claim 1, wherein the computing device is configured to determine a scan setting of the confocal imaging device based on the circularly asymmetric image pattern received by the image sensor.

5. The intraoral scanning device of claim 1, wherein the confocal imaging device comprises a cylindrical lens.

6. The intraoral scanning device of claim 1, wherein the confocal imaging device comprises a lens having a toroidal surface.

7. The intraoral scanning device of claim 1, wherein the confocal imaging device comprises a substantially flat window having a major surface positioned oblique to the light path.

8. The intraoral scanning device of claim 1, wherein the predetermined astigmatic aberration is associated with a lens adjacent to a light source of the confocal imaging device.

9. A system, comprising:
a hand-held intraoral scanner, comprising:
a hand-held housing;
a confocal imaging device disposed in the hand-held housing, the confocal imaging device having a predetermined astigmatic aberration disposed in a light path thereof to asymmetrically focus light in a predetermined manner, wherein the light is associated with an image of a portion of an object captured by the confocal imaging device; and
an image sensor disposed within the hand-held housing, the image sensor comprising a plurality of pixels, wherein the plurality of pixels are to receive the light associated with the image of the portion of the object, the light having a circularly asymmetric image pattern; and a computing device to:
process the image of the portion of the object captured by the confocal imaging device; and
determine a positional relationship between the portion of the object and a focus plane of the confocal imaging device based on a diffraction pattern over a portion of the plurality of pixels, wherein the diffraction pattern is associated with the circularly asymmetric image pattern.

10. The system of claim 9, wherein the predetermined astigmatic aberration is associated with a lens of the confocal imaging device that is adjacent to the image sensor.

11. The system of claim 9, wherein the computing device is configured to determine a distance between the confocal imaging device and the object based on the circularly asymmetric image pattern received by the image sensor.

12. The system of claim 9, wherein the computing device is configured to determine a scan setting of the confocal imaging device based on the circularly asymmetric image pattern received by the image sensor.

13. The system of claim 9, wherein the computing device is external to the hand-held housing.

14. The system of claim 9, wherein the confocal imaging device comprises a cylindrical lens.

15. The system of claim 9, wherein the confocal imaging device comprises a lens having a toroidal surface.

16. The system of claim 9, wherein the confocal imaging device comprises a substantially flat window having a major surface positioned oblique to the light path.

17. The system of claim 9, wherein the predetermined astigmatic aberration is associated with a lens adjacent to a light source of the confocal imaging device, wherein the light source is disposed within the hand-held housing.

18. The intraoral scanning device of claim 1, further comprising the computing device to:
determine, from the circularly asymmetric image pattern, a first length along a first axis and a second length along a second axis that is perpendicular to the first axis;
determine a ratio of the first length to the second length; and
determine a distance between the confocal imaging device and the object based at least in part on the ratio.

19. The system of claim 9, further comprising the computing device to:
determine, from the circularly asymmetric image pattern, a first length along a first axis and a second length along a second axis that is perpendicular to the first axis;
determine a ratio of the first length to the second length; and
determine a distance between the confocal imaging device and the object based at least in part on the ratio.

* * * * *